(12) United States Patent  (10) Patent No.: US 8,233,986 B2
Deininger et al.  (45) Date of Patent: Jul. 31, 2012

(54) CONNECTOR HEADER FOR IMPLANTABLE MEDICAL DEVICE

(75) Inventors: Steve T. Deininger, Blaine, MN (US); Jeffrey J. Clayton, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 1418 days.

(21) Appl. No.: 11/776,653

(22) Filed: Jul. 12, 2007

(65) Prior Publication Data

US 2009/0018601 A1  Jan. 15, 2009

(51) Int. Cl.
*A61N 1/375* (2006.01)
(52) U.S. Cl. .......................... 607/37; 439/909
(58) Field of Classification Search .............. 607/36–38; 439/909
See application file for complete search history.

(56) References Cited

U.S. PATENT DOCUMENTS

| | | | |
|---|---|---|---|
| 6,115,634 A | 9/2000 | Donders | |
| 6,574,508 B2 | 6/2003 | Zaouali | |
| 2003/0163171 A1 | 8/2003 | Kast et al. | |
| 2004/0093038 A1* | 5/2004 | Biggs et al. | 607/37 |
| 2004/0116976 A1 | 6/2004 | Spadgenske | |
| 2006/0167534 A1 | 7/2006 | Malinowski | |
| 2007/0087637 A1 | 4/2007 | Zart | |

FOREIGN PATENT DOCUMENTS

| | | |
|---|---|---|
| WO | WO 2003/034892 | 5/2003 |
| WO | WO 2006/105463 | 10/2006 |

OTHER PUBLICATIONS

PCT Search Report dated Dec. 3, 2008.

* cited by examiner

*Primary Examiner* — Carl H Layno
*Assistant Examiner* — Jessica Sarcione

(57) ABSTRACT

A connector header includes a housing formed from a plastic material having a modulus of rigidity of 100 ksi or greater. The housing defines an opening for insertion of a lead. The connector header further includes a lead receptacle having an electrically conductive element. The electrically conductive element is operably couplable to a feedthrough of the implantable medical device. The lead receptacle is in communication with the opening and is disposed within the housing such that an electrical contact of the lead is electrically couplable to the conductive element of the receptacle when the lead is inserted into the receptacle.

22 Claims, 14 Drawing Sheets

CONNECTOR HEADER FOR IMPLANTABLE MEDICAL DEVICE

FIELD

This disclosure relates, inter alia, to implantable medical devices. More particularly, it relates to connector headers that operably couple medical leads to medical devices.

BACKGROUND

Many implantable medical devices, such as neurostimulators, pacemakers and defibrillators, transmit electrical signals to provide therapy to a patient. Electrical signals generated by the devices may be delivered to the patient tissue via electrodes disposed at a distal portion of a medical lead. The lead is electrically coupled to the device via a connector block or header of the device. The connector header includes a receptacle for insertion of the lead.

Typically, pins, which are electrically coupled to electronics of the device, are fed through a hermetically sealed housing of the device. The receptacle of the connector header contains conductive elements that are electrically coupled to the pins. The lead is insertable into the receptacle such that electrical contacts of the lead may be electrically coupled to the conductive elements of the receptacle. Conductors electrically couple the contacts of the lead to the electrodes.

Typical connector headers include a polyurethane housing and are made generally as follows. The lead receptacles are placed into the molded polyurethane housing, or alternatively, are placed into a polysulfone or other rigid polymeric frame over which the polyurethane housing is placed. Adhesive is used to bond the receptacles to the housing, the conductive elements of the receptacles are welded to the feedthrough pins, and the housing is then filled with liquid silicone rubber at low temperature and pressure. Low temperature conditions are used because polyurethane is temperature sensitive, and low pressure is to prevent distortion of the lead receptacles under during over-molding with liquid silicone rubber. Under such conditions, over-molding with liquid silicone molding takes a significant amount of time. The connector header housing is then secured to the housing of the device by inserting a barbed fastener through a bracket in the device housing and a molded hole in the polyurethane housing of the connector header.

Polyurethane, having a modulus of about 26 ksi, serves as a suitable material for a connector header housing because it does not tend to crack or craze under stresses associated with being implanted within a patient. For example, stress associated with connection of the header to the housing of the device via the barbed fastener is well tolerated by polyurethane housings. However, due to the lack of rigidity of polyurethane housings, stress associated with side-to-side deflection of the connector header relative to the device may be transferred to the feedthrough pins, resulting in feedthrough failure. More rigid polymeric materials have not been used because they are prone to cracking and crazing.

SUMMARY

The present disclosure describes, inter alia, systems, devices that employ connector headers having more rigid, dimensionally stable housings and methods for manufacturing connector headers.

In an embodiment, a connector header for an implantable medical device is described. The connector header includes a housing formed from a plastic material having a modulus of rigidity of 100 ksi or greater. The housing defines an opening for insertion of a lead. The connector header further includes a lead receptacle having an electrically conductive element. The electrically conductive element is operably couplable to a feedthrough of the implantable medical device. The lead receptacle is in communication with the opening and is disposed within the housing such that an electrical contact of the lead is electrically couplable to the conductive element of the receptacle when the lead is inserted into the receptacle.

In an embodiment, an implantable medical device including a connector header is described. The implantable medical device has a housing, and electronics are disposed within the housing. An electrical feed through element is operably coupled to the electronics and extends through a wall of the housing. The connector header includes a header housing formed from a plastic material having a modulus of rigidity of 100 ksi or greater. The header housing defining an opening for insertion of a lead. The header further includes a lead receptacle having an electrically conductive element operably coupled to the feedthrough element. The lead receptacle is in communication with the opening and is disposed within the header housing such that an electrical contact of the lead is electrically couplable to the electrically conductive element of the receptacle when the lead is inserted into the receptacle.

By providing devices, systems having more rigid dimensionally stable housings, the housings may be manufactured more quickly and easily, with tighter tolerances. Implantable medical devices employing such rigid connector housings can also result in reduced feedthrough failure. These and other advantages will be readily understood from the following detailed descriptions when read in conjunction with the accompanying drawings.

Figure 1:
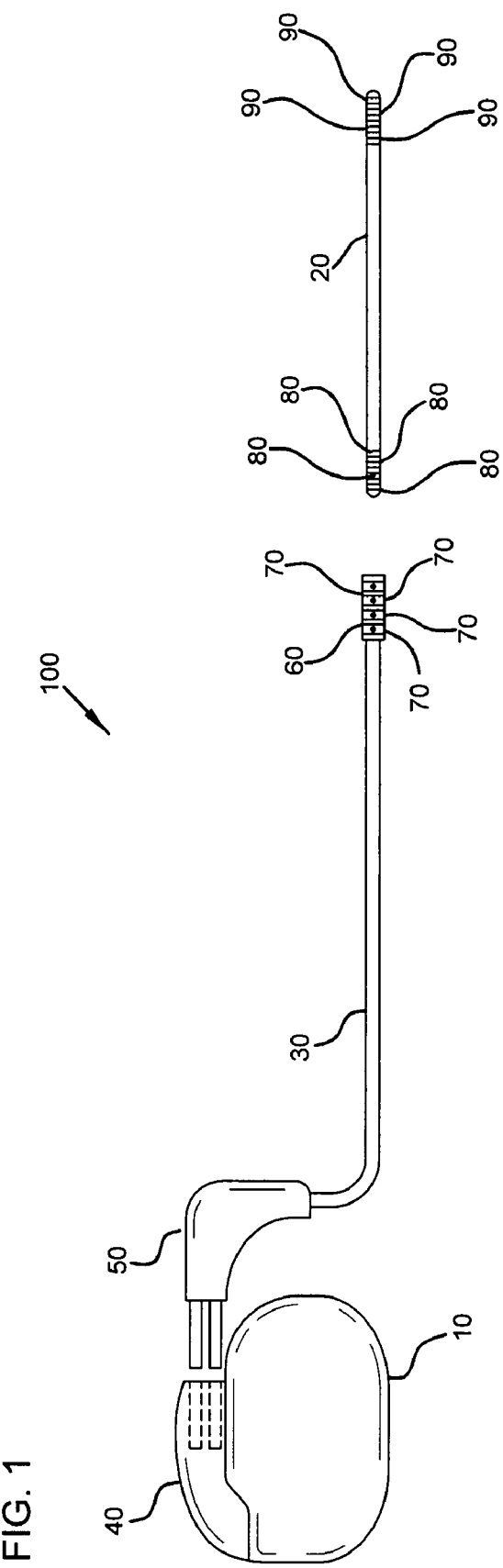
FIG. 1 is a diagrammatic representation of an exploded view of a representative neurostimulation system.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used herein, "ksi" means kilopounds per square inch.

"Couplable" as used herein, means capable of being coupled.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, connection headers formed of rigid plastic material and devices and systems including such headers. Suitable rigid plastics include plastics having a modulus of rigidity of 100 ksi or greater, such as high temperature ($T_g$) plastics, including polysulfone, polycarbonate, polyether ether ketone, polyether amide and the like. In various embodiments the rigid plastics have a modulus of rigidity in the range of 100 ksi to 400 ksi, 200 ksi or greater or 300 ksi or greater. Such rigid plastics tend to be subject to cracking and crazing, particularly at body temperature and have not been used in implantable medical devices for components subject to stress. One way to reduce stress is to reduce molded-in stress by molding at a high temperature, e.g. near the annealing temperature of the polymer. For polysulfone, holding the mold temperature between 300° F. and 350° F. may be sufficient. Minimizing applied stress is also desirable for such rigid plastics. In addition, such rigid plastics often do not adhere well to medical adhesives. As such, it may be desirable to plasma treat, siloxane coat, or otherwise treat surfaces of the rigid plastic material to which adhesive may be applied.

By reducing molded-in stresses and minimizing applied stresses, it has been found that connector headers made of rigid plastic produce several advantages. For example, because of the rigidity of the plastic, connector headers can be made more dimensionally stable, resulting in tighter manufacturing tolerances and allowing for better fit and alignment of lead receptacles in the housing of the connector, which can result in easier insertion of a lead into the receptacle. The rigidity of the housing has also been found to result in less feed through failure relative to conventional headers employing polyurethane housings.

The teachings presented herein are applicable to any implantable medical device system employing a device having electronics, an apparatus for carrying electrical signals from the electronics to the patient, from the patient to the electronics, or the like, and a connector header for operably coupling the apparatus to the device. For example, the apparatus may include a sensor for providing signals to the electronics or may include an electrode for delivering electrical signal to the patient. For the sake of convenience, the device may often be described as an implantable electrical signal generator but it will be understood that the device may be any suitable device, including, for example, a monitoring device.

Referring to FIG. 1, an exploded view of an embodiment of a representative system 100 is shown. The system 100 includes an implantable electrical signal generator 10, a lead extension 30 and a lead 20. Implantable electrical signal generator 10 includes a connector header 40 configured to receive plug 50 at proximal end of lead extension 30 or other adaptor to couple lead 20 to electrical signal generator 10. The distal end portion of lead extension 30 includes a connector 60 configured to receive proximal end portion of lead 20. Connector 60 includes internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown). In general, a lead 20 may include any number of electrodes 90, e.g. one, two, three, four, five, six, seven, eight, or sixteen. Typically, each electrode 90 is electrically coupled to a discrete electrical contact 80. While not shown, it will be understood that more than one lead 20 may be operably coupled to one electrical signal generator 10 or one extension 30 or that more than one extension 30 may be operably coupled to one electrical signal generator 10. It will be further understood that lead 20 may be coupled to electrical signal generator 10 without use of extension 30 or adaptor.

Figure 2A:
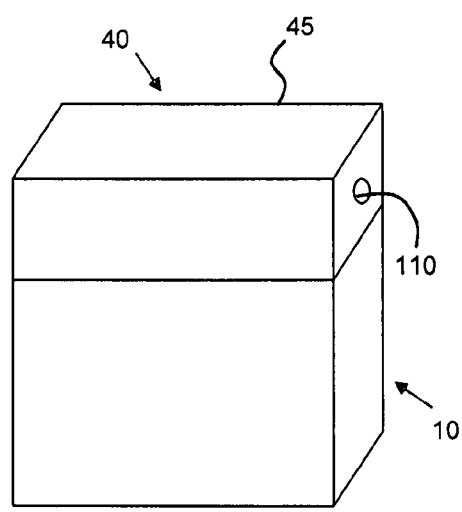
FIGS. 2A-D are schematic drawings of perspective views of representative devices with associated connection headers.
Figure 2B:
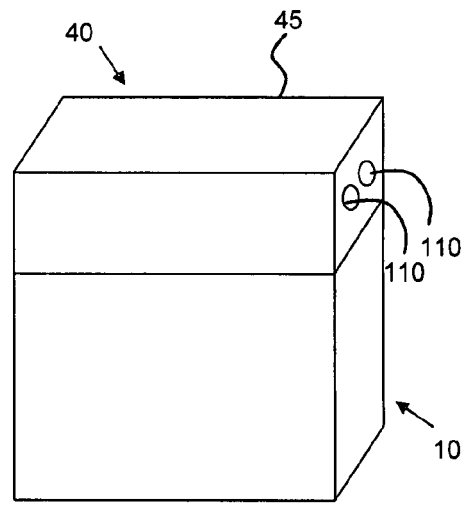
Figure 2C:
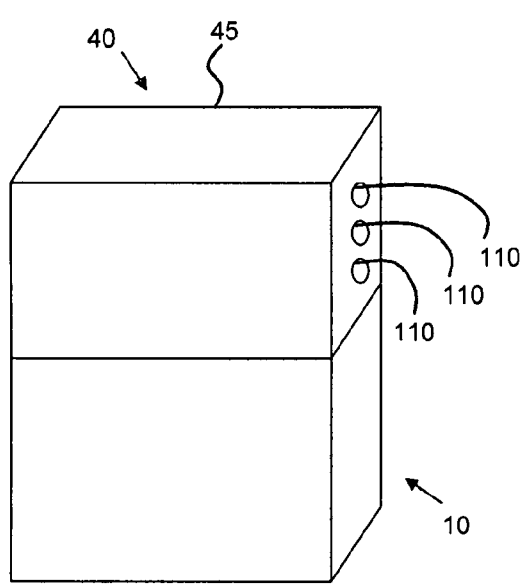

As shown in the embodiments depicted in FIGS. 2A-C, connector header 40 may include any number of openings 110 defined by header housing 45 for receiving lead, lead extension, adaptor, or the like. Openings 110 may be arranged in any suitable orientation with respect to connector header 40 or device 10.

Figure 2D:
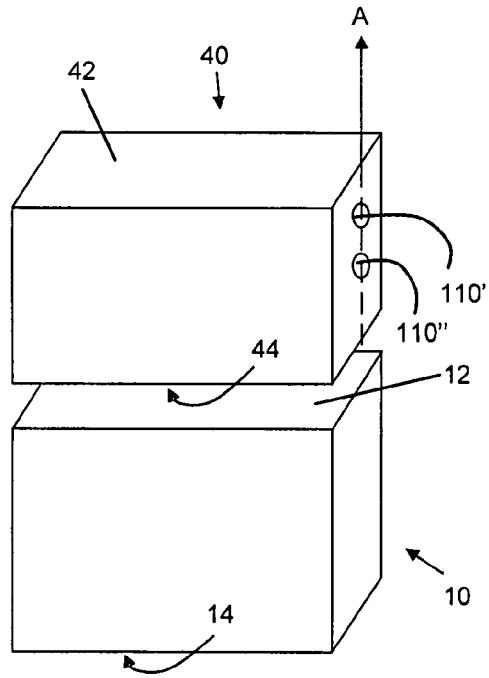

Referring to the view in FIG. 2D in which header 40 is removed from device 10, device 10 has a top 12 and bottom 14 surface and header 40 has a top 42 and bottom 44 surface. At least a portion of bottom surface 44 of header 40 is disposed on at least a portion of top surface 12 of device 10 when header 40 is connected to device 10. A longitudinal axis A runs through header 40 from bottom to top. In various embodiments, header housing 45 has a first opening 110' configured to receive a lead (not shown in FIG. 2D) and a second opening 110" configured to receive a lead and disposed between the first opening 110' and the bottom surface 44 of the header 40. In some embodiments, first and second openings 110', 110" are disposed along the longitudinal axis A.

Figure 3:
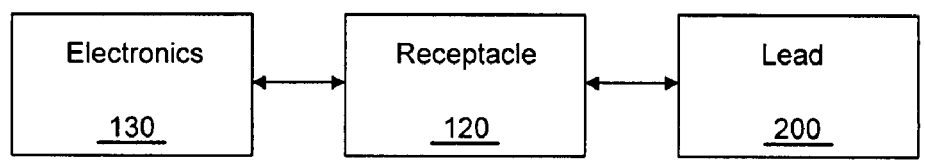
FIG. 3 is a block diagram of a system showing a connector header receptacle operably coupling electronics of a device to a lead.

Referring to FIG. 3, a block diagram of a representative system is shown. Generally, receptacle 120 operably couples a lead 200 to electronics 130 of implantable device. For the sake of convenience, lead 200 will be used hereinafter to refer to lead 20, lead extension 30, or adaptor configured to couple lead 20 or extension 30 to receptacle 120 in connector header 40, as well as any apparatus that may be used to carry an electrical signal to or from device 10.

Figures 4A, 4B:
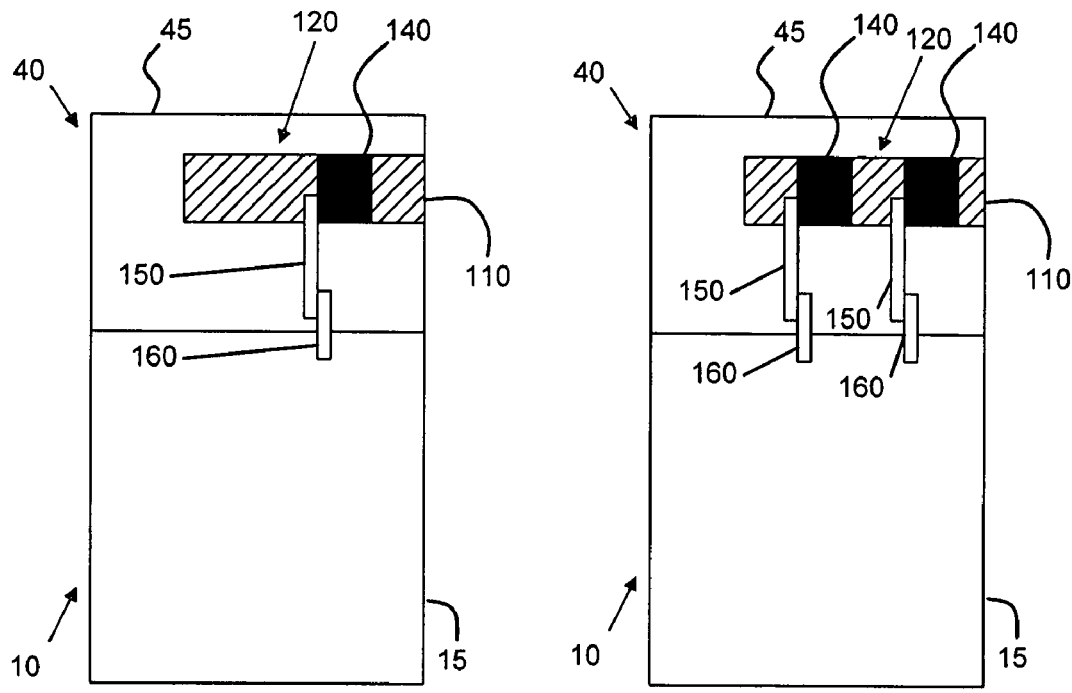
FIGS. 4A-B are schematic cross sections showing portions of devices and connector headers.

Referring to FIGS. 4A-B, schematic cross sections of embodiments of devices are shown. In the embodiments depicted in FIGS. 4A-B, receptacle 120 is axially aligned with and in communication with opening 110 of connector header 40. The lead receptacle 120 includes an electrically conductive element 140 positioned in header 40 such that an electrical contact of a lead may be electrically coupled to conductive element 140 when the lead is inserted into the receptacle 120. Conductive element 140 is operably coupled to electronics 130. As shown in FIGS. 4A-B, a conductor 150 may be connected to conductive element 140 and to feedthrough 160 projecting through housing 15 of device 10. Feedthrough 160 is operably coupled to electronics (not shown in FIG. 4) of device 10. FIG. 4A shows a receptacle 120 having one conductive element 140, and FIG. 4B shows a receptacle 120 having two conductive elements 140. Of course, receptacle 120 may include any suitable number of conductive elements 140. It will be understood that connection header 40 may include any suitable number of lead receptacles 140, typically corresponding to the number of openings 110 defined by housing 45 of header 40.

Figure 5A:
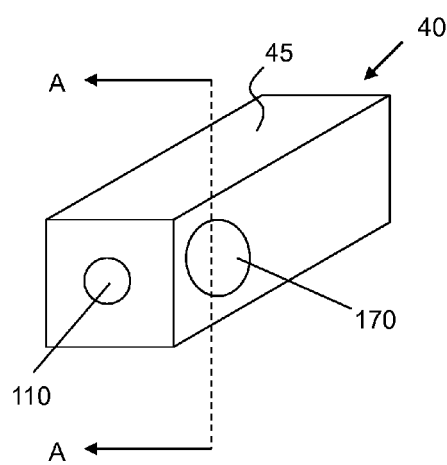
FIG. 5A is a schematic diagram of a perspective view of a representative connector header.
Figure 5B:
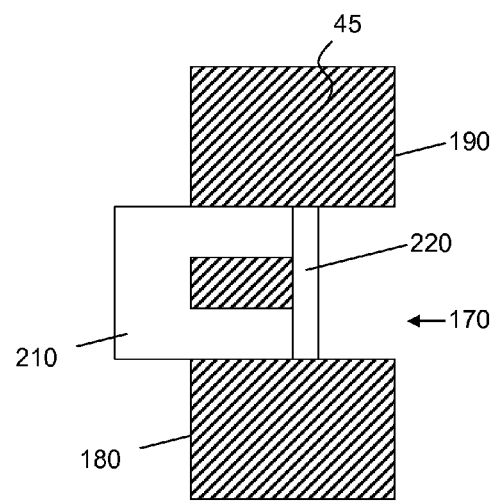
FIGS. 5B-D are schematic drawings of cross sections taken along line A-A of FIG. 5A, showing portions of the header according to various embodiments.
Figure 5C:
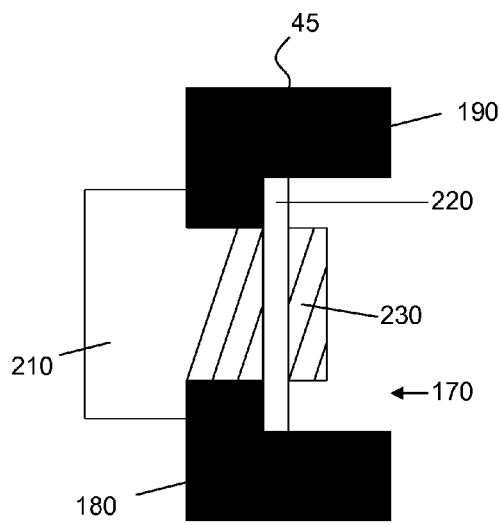
Figure 5D:
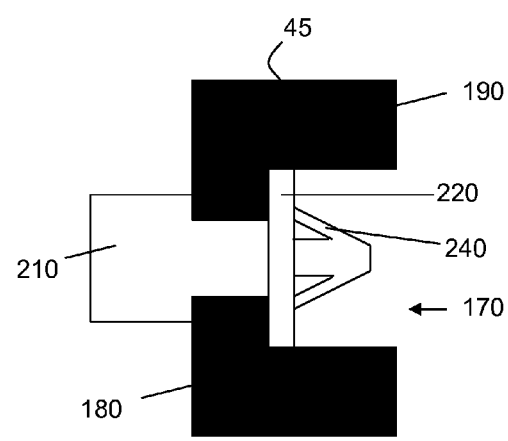

Referring to FIG. 5A, a perspective view of an embodiment of a connector header 40 is shown. A side opening 170 is defined by housing 45 of header 40. FIGS. 5B-D are schematic cross sections taken through line A-A as shown in FIG. 5A of embodiments of header 40. As shown in the embodiments depicted in FIGS. 5B-D, side opening 170 extends from an interior surface 180 to an exterior surface 190 of housing 45. At least a portion of receptor anchor element 210 extends into the side opening 170. A securing element 220 located external to header housing 45 is operably coupled to anchor element 210. In the embodiment depicted in FIG. 5B, securing element 220 is a washer and may be connected to anchor element 210 by welding, adhesive, or other suitable means. In the embodiment depicted in FIG. 5C, securing element 220 is a nut and anchor element 210 includes a threaded bolt portion 230. Securing element nut 220 may be screwed onto threaded bolt portion 230 of anchor element 210. In the embodiment depicted in FIG. 5D, securing element 220 is a washer or the like, and anchor element 210 includes barbs 240 or tines that may be inserted through a hole in securing element 220 to secure anchor element 220 relative to housing 45. Receptor anchor element 210 is operably coupled to receptacle (not shown in FIGS. 5A-D) and secures the lead receptacle to the connector header housing 45. It will be understood that other anchor element 210 and securing element 220 designs may be employed.

Figure 6A:
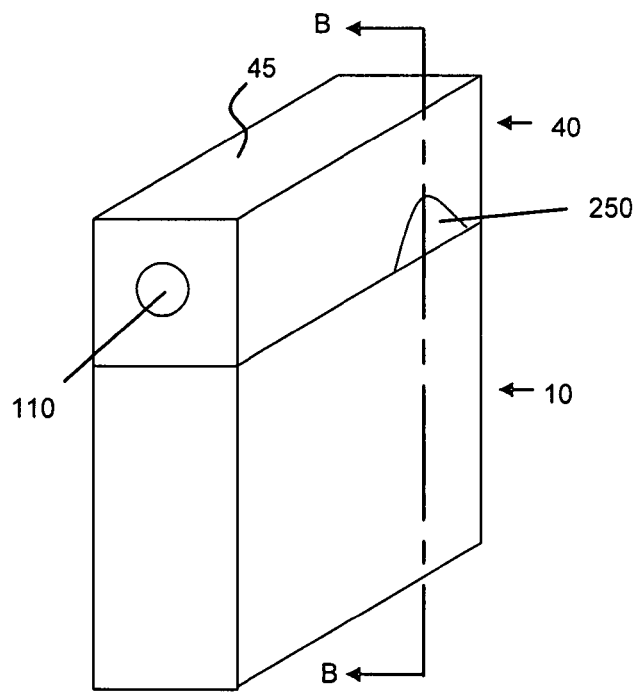
FIG. 6A is a schematic diagram of a perspective view of a representative connector header and associated device.
Figure 6B:
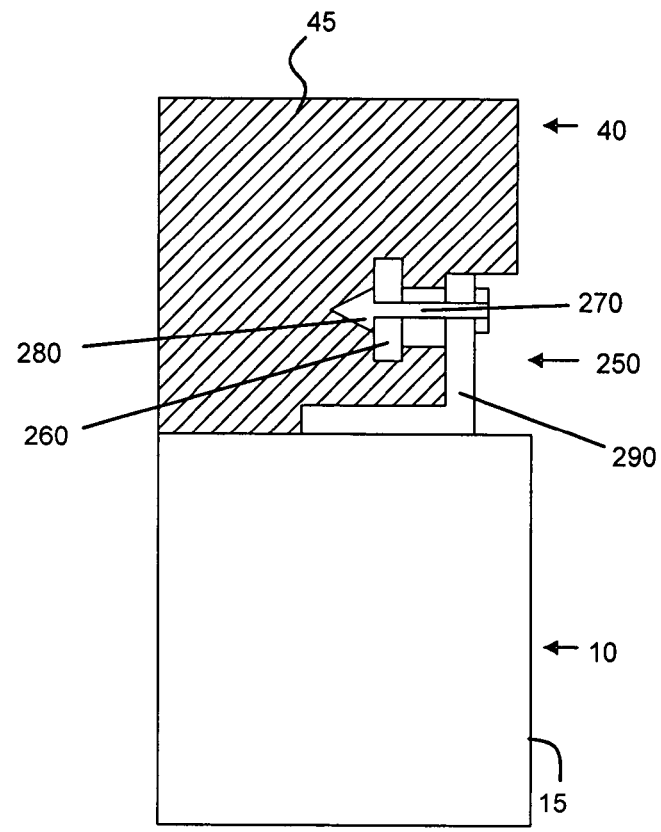
FIG. 6B is a schematic cross section taken along line B-B of FIG. 6A showing portions of the header and device.

Referring to FIG. 6, a representative embodiment of a device is shown. FIG. 6A is a perspective view of a connector header 40 connected to device 10. Housing 45 of header 40 includes a side hole 250. FIG. 6B is a schematic cross section of the device taken along the line B-B shown in FIG. 6A. As shown in FIG. 6B, header 40 may include a reinforcement member 260 for connecting or coupling header 40 to device 10. The reinforcement member 260 is positioned in header 40 such that header 40 may be operably coupled to the device 10. In the embodiment depicted in FIG. 6B, connector header 40 is connected to device 10 with a fastener 270, such as a nail or pin, having barbs 280 or tines. The barbs 280 of the fastener 270 are inserted first through a bracket 290 attached to housing 15 of device 10 and then through a reinforcement member 260 molded into header housing 45. Of course any suitable means for connecting or coupling reinforcement member 260 to bracket 290 may be employed, including e.g. those discussed with regard to FIGS. 5A-D. It will be understood that header 40 may include more than one side hole 250 and more than one reinforcement member 260 and may be attached to device at multiple locations, e.g. via multiple brackets 290. Reinforcement member 260 serves to transfer applied stresses that would be applied to housing 45 in traditional header configurations to reinforcement member 260, bracket 290 and device housing 15. Reinforcement member 260 is preferably made of a material that is sufficiently rigid to securely anchor header 40 to device 10, but that is sufficiently flexible to prevent transferring excessive stress to housing 45, which may result in undesired cracking or crazing.

Figure 7:
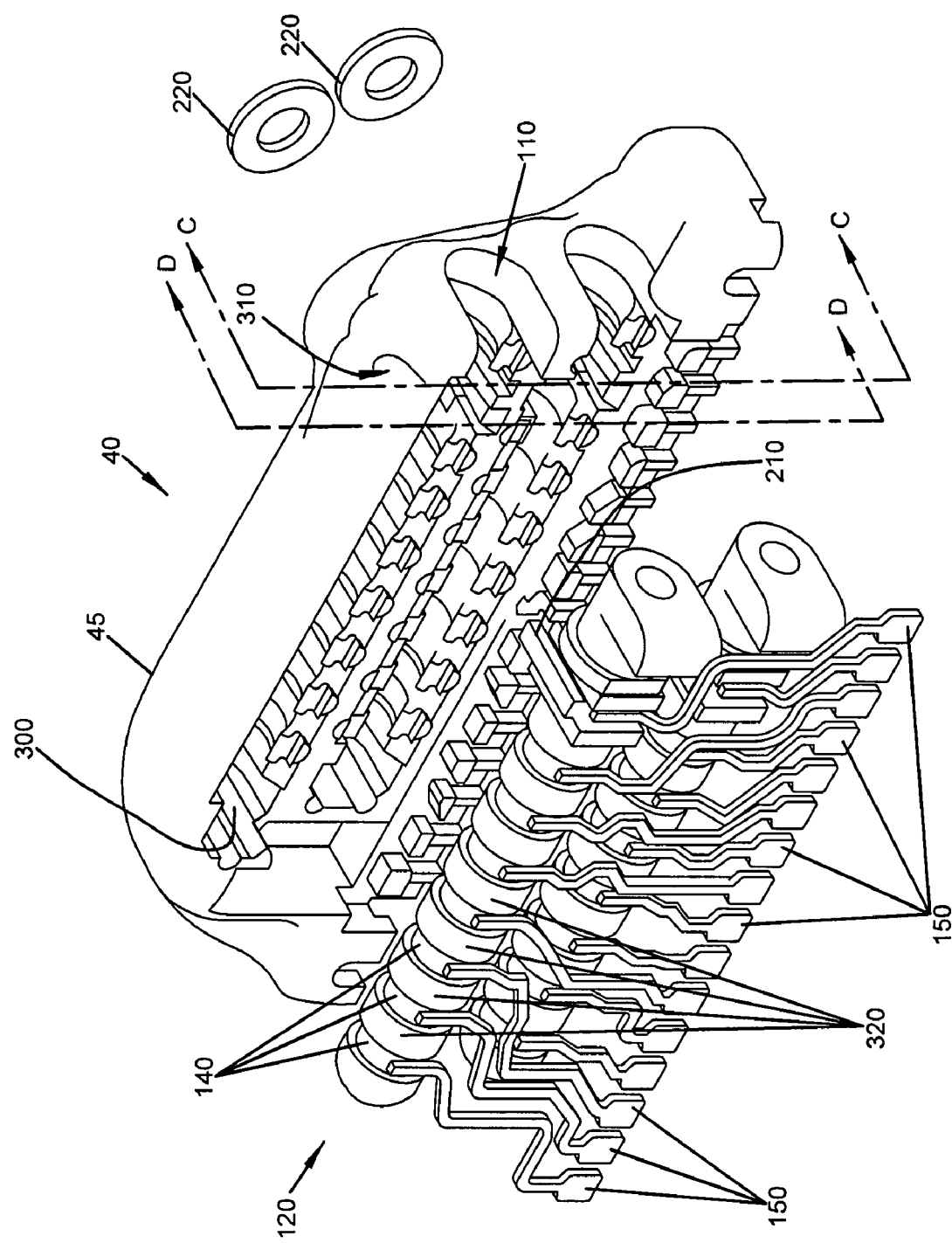
FIG. 7 is an exploded perspective view of portions of a representative connector header.

Referring to FIGS. 7-11, an embodiment of a connector header 45 is shown. FIG. 7 is an exploded view of a portion of connector header 40 showing housing 45, lead receptacles 120 and securing elements 220. A portion of the interior surface of housing 45 defines recesses 300 configured to receive lead receptacles 120. Lead receptacle 120 includes alternating conductive elements 140 and non-conductive insulating elements 320. Lead receptacle 120 may be formed according to any known or future developed process. Typically lead receptacle 120 will include a plurality of subunits including an electrically insulating ring disposed between an electrically conductive contact ring and an attachment ring or electrically conductive space ring (collectively, conductive element 140).

Conductors 150 configured to electrically couple conductive elements 140 to feedthrough pins (not shown in FIG. 7) are electrically connected, e.g. welded, to conductive elements 140. Conductors 150 may be made of any suitable material, such as platinum, platinum iridium, titanium, tantalum, nickel-cobalt-molybdenum alloys, and the like and may be molded, stamped or otherwise formed. In the embodiment depicted in FIG. 7, anchor element 210 is incorporated into lead receptacle 120 and serves as a conductive element configured to be electrically coupled to a contact of a lead when the lead is inserted into the receptacle 120. As with conductors 150, conductive anchor element 210 is preferably formed from an electrically conductive biocompatible material. Of course anchor element 210 may be a composite material, and in embodiments where anchor element is does not serve as a conductive element of a receptacle 120, anchor element 210 may be formed of non-conductive material. In the embodiment depicted in FIG. 7, conductor 150 is electrically connected to anchor element 210 and is configured to couple anchor element 210, serving as a conductive element of lead receptacle 120, to feedthrough pins of associated device. A suture hole 310 defined by housing 45 may be included in connector header 40 for securing header 40 and associated device at a location in a patient.

Figure 8:
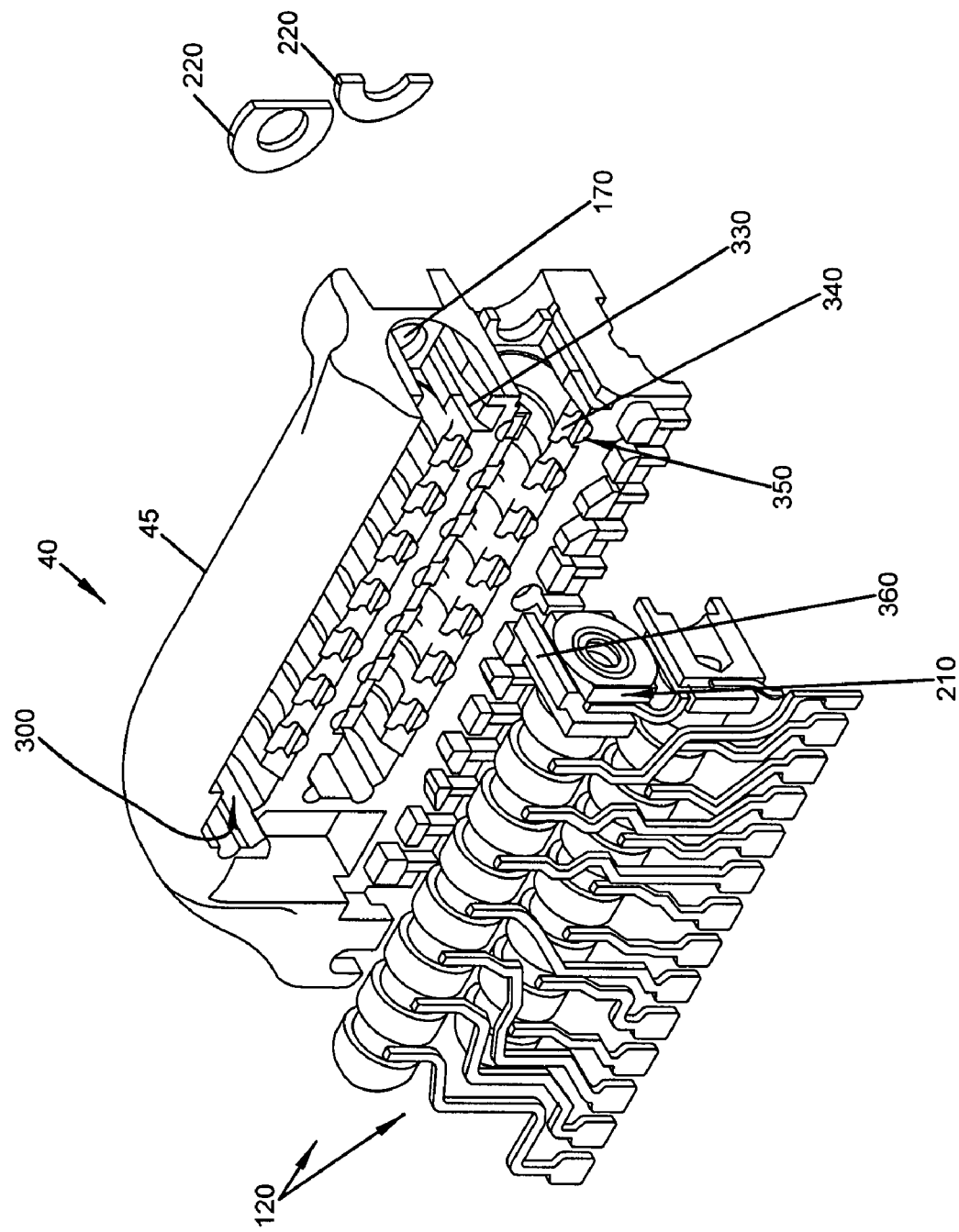
FIG. 8 is an exploded perspective view of the header shown in FIG. 7 with a section taken at line C-C.
Figure 9:
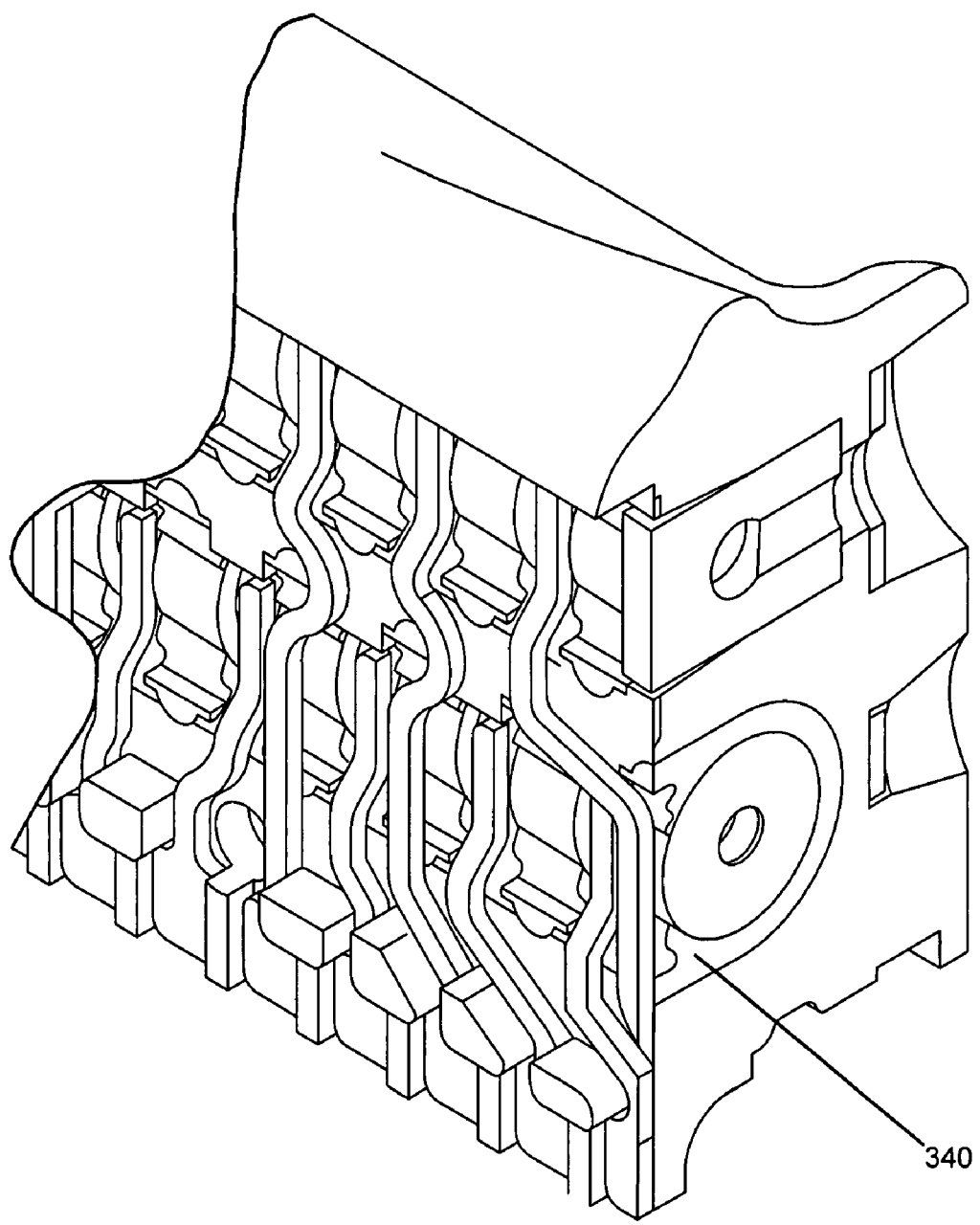
FIG. 9 is a perspective view of the header shown in FIG. 7 with a section taken at line D-D.

FIG. 8 is an exploded view of a schematic of a portion of the connector header 40 shown in FIG. 7 with a section taken along line C-C. Securing element 220 depicted in FIG. 8 is a washer that may be welded to legs of anchor element 210. As shown in FIG. 8, a portion of the interior surface of the housing 45 (in this instance, the recess portion 300) contains a groove 330 configured to receive a complementary raised feature 360 of anchor element 210. Of course, anchor element 210 may contain a groove and housing 45 may contain a protruding feature. Any combination of complementarily configured features may be employed or no such features may be included. However, such complementary mating features facilitate alignment of lead receptacle 120 with header 40 and distribute torsional stress from the point of the weld, particularly with the tighter tolerances that can be obtained with rigid plastic material. Recess 300 includes channels 350 into which adhesive 340 may be applied to assist in retaining lead receptacle 120 in the recess. The adhesive 340 may also serve to further electrically isolate conductive portions of receptacles 120. It will be understood that other nonconductive materials, such as liquid silicone rubber, may be overmolded to achieve a similar electrical isolation effect. FIG. 9 is a perspective view of a section of the connector header 40 shown in FIG. 7, with adhesive 340 being more clearly shown. As medical adhesives may not adhere well to rigid plastics, it may be desirable to plasma-treat, siloxane-coat, or otherwise treat a surface of the plastic material to which adhesive is to bind.

Anchor element 210 may serve as a set screw block (e.g., see embodiment depicted in FIG. 5B). A set screw (not shown) may be inserted through securing element 220 washer and tightened to secure lead within receptacle 120 when inserted into the receptacle. A plug or grommet (not shown), e.g. a silicone plug, may be placed externally into side hole 170. Such a plug or grommet can serve to electrically isolate anchor element 210 from patient tissue or body fluid when the device is implanted in the patient in embodiments where anchor element 210 serves as a conductive element of receptacle 120.

Figure 10:
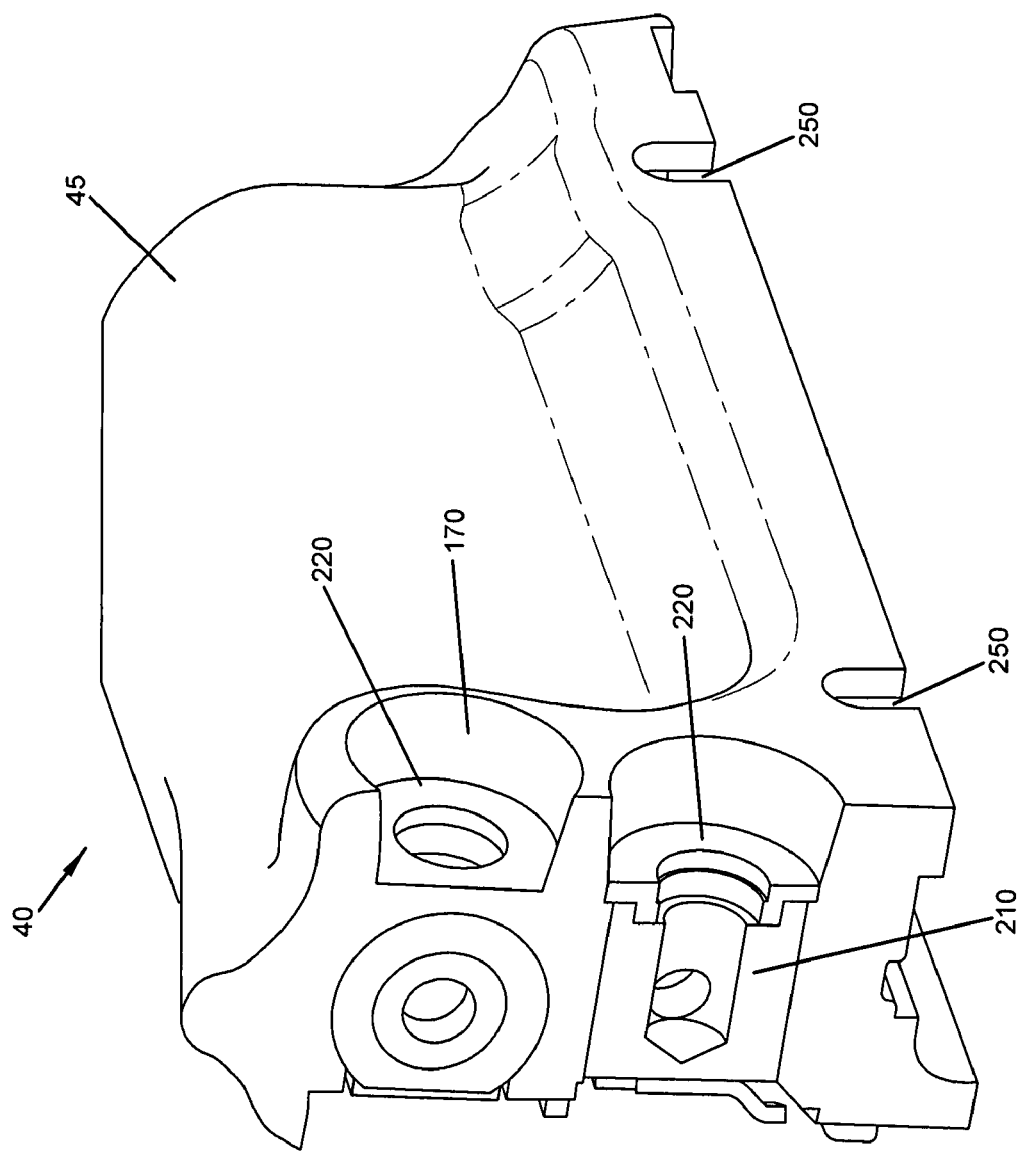
FIG. 10 is an isometric view of the header shown in FIG. 7 with a section taken at line C-C.

FIG. 10 is an isometric view of a section of the connection header 40 shown in FIG. 7. FIG. 10 shows side holes 170, 250 formed in housing 45. Securing element 220 (washer) is welded to anchor element 210 and secures anchor element 210 against housing 45. Side holes 250 provide access for connecting header 40 to device (not shown in FIG. 10).

Figure 11:
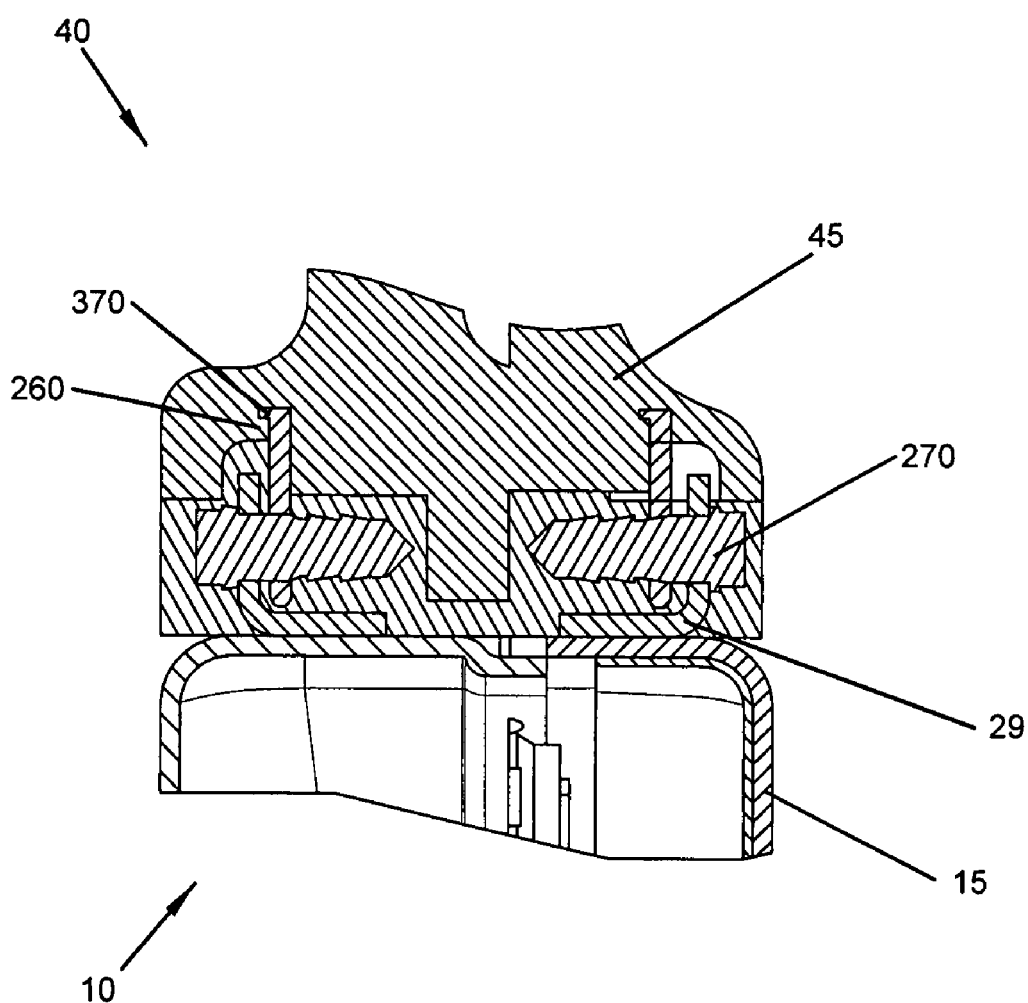
FIG. 11 is a schematic cross section of a portion of a header and associated device.
Figure 12:
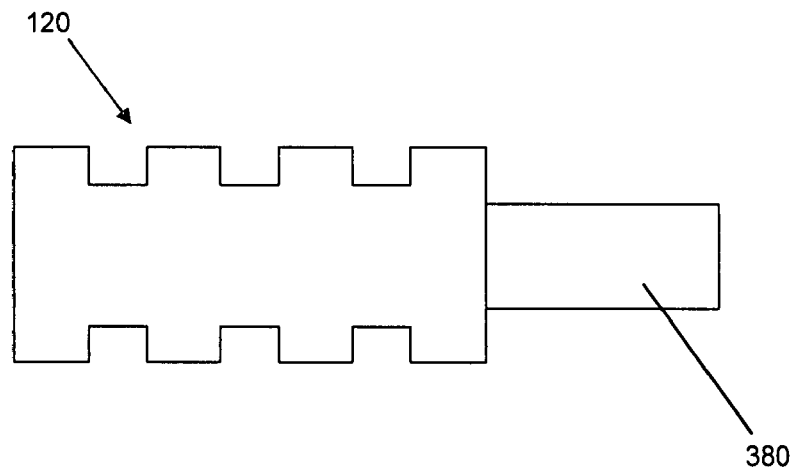
FIG. 12 is a diagrammatic representation of a side view of a representative lead receptacle disposed about an alignment pin.

Referring to FIG. 11, a cross section of a portion of a connector header 40 as depicted in FIG. 7 is shown connected to device 10. Reinforcement member 260 is molded into header housing 45 and includes a lip 370 to facilitate retaining reinforcement member 260 in housing 45. Reinforcement member 260 has a hole (not shown) through which fastener 270 may be inserted. The hole of reinforcement member 260 is axially aligned with a hole in bracket 290 attached to housing 15 of device 10 when connector header 40 is connected to device 10 by fastener 270. Fastener 270, bracket 290, and reinforcement member 260 may be made of any suitable material or combination of materials. In an embodiment, fastener 270, bracket 290, and reinforcement member 260 are made of titanium.

Figure 13:
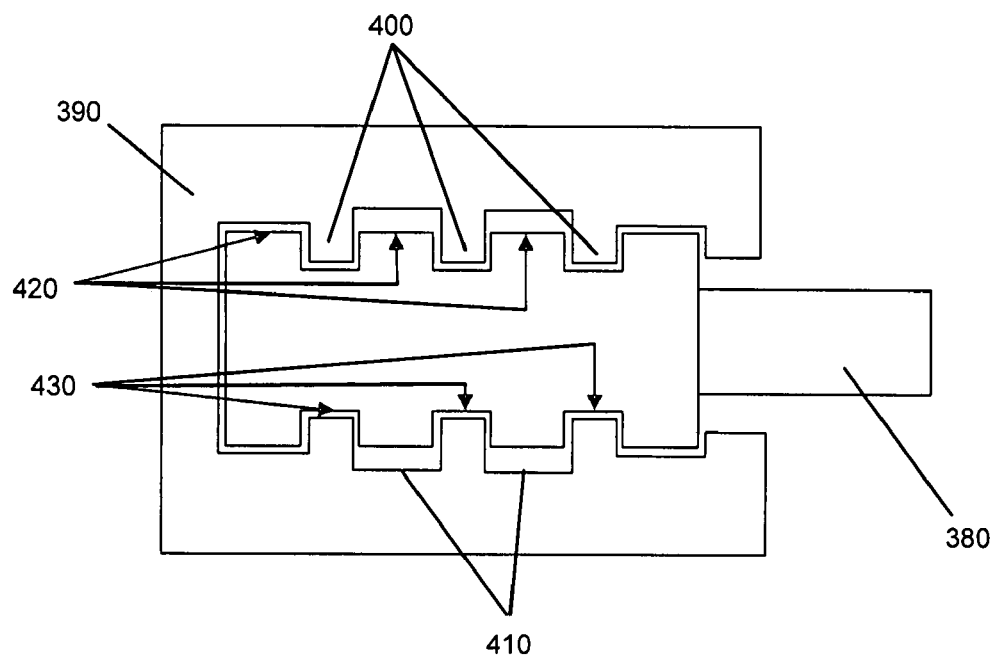
FIG. 13 is a diagrammatic representation of a side view of a representative lead receptacle disposed about an alignment pin with the lead receptacle placed in a restraining fixture.

Any suitable method may be employed to manufacture connector headers 40 and devices 10 including connector headers 40 as described herein. A representative method is discussed below with reference to FIGS. 12-16. In an embodiment, lead receptacles 120 are assembled or constructed on alignment pins 380 or mandrels (500). Lead receptacles 120 typically include alternating conductive and non-conductive portions (see, e.g., FIG. 14). The lead receptacles 120 constructed on the alignment pins 380 are placed on a restraining fixture 390 (510) configured to engage an exterior surface of lead receptacle 120 and maintain alignment of lead receptacle 120 (see, e.g., FIG. 13). The restraining fixtures 390 depicted in FIGS. 13-14 has raised 400 have and recessed 410 features complementary to raised 420 and recessed 430 portions of receptacle 120. In the embodiment depicted in FIG. 13, the raised exterior portions 420 of receptacle 120 correspond to non-conductive insulating portions 320, and the recessed portions 430 correspond to conductive portions 140. A lead frame pin assembly 440 is attached and electrically coupled, e.g. by welding, to conductive portions 140 of lead receptacle 120 (520) while the receptacles 120 are engaged by restraining fixture 390.

Figure 14:
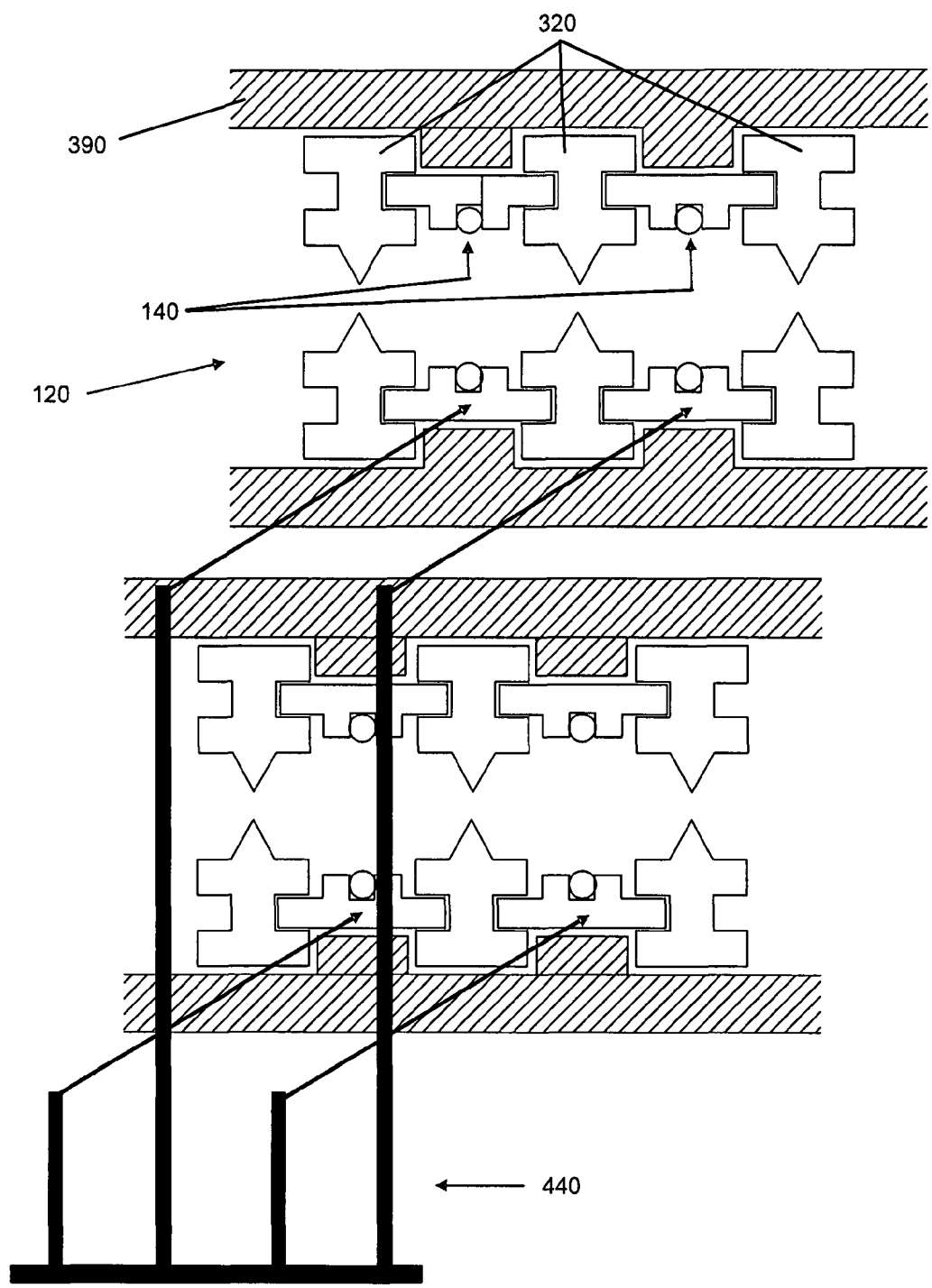
FIG. 14 is a diagrammatic representation of a cross section of representative lead receptacle components in a restraining fixture and an exploded lead frame pin assembly.
Figure 15:
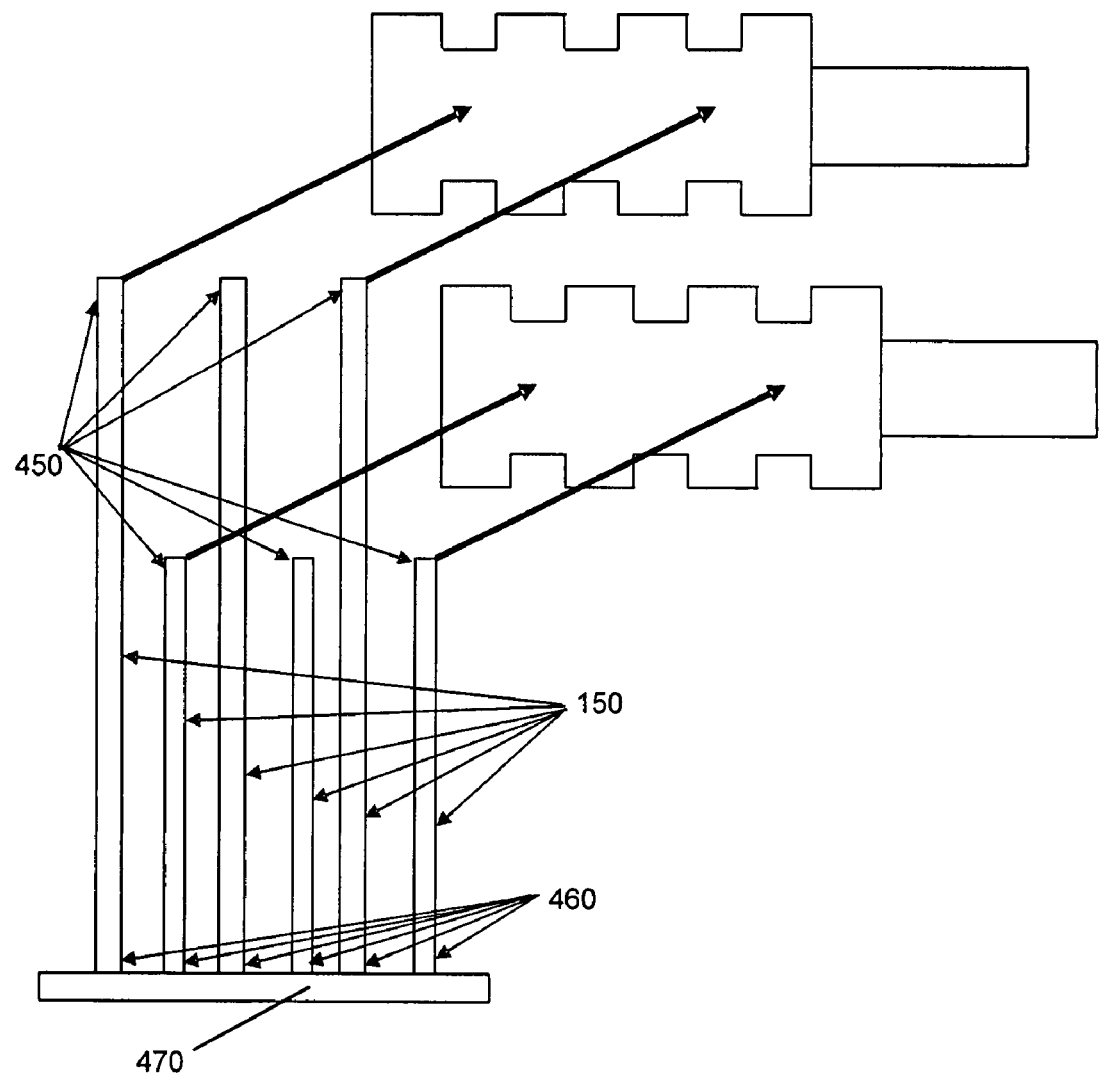
FIG. 15 is a perspective view of a representative lead receptacle and alignment pin and an exploded lead frame pin assembly.
Figure 16:
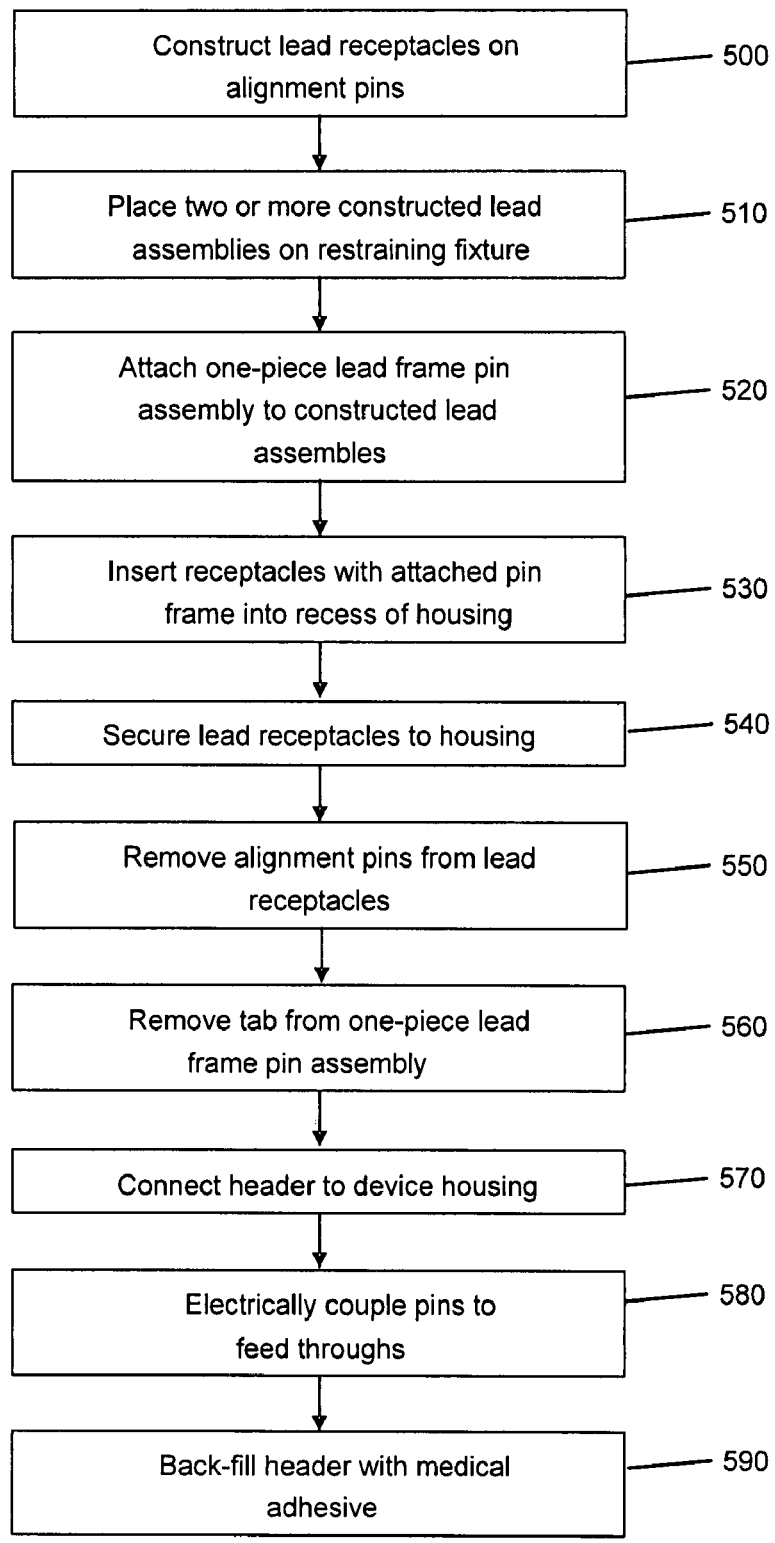
FIG. 16 is a flow diagram of a representative method.

The lead frame pin assembly 440 shown in FIGS. 14-15 is a one-piece assembly having conductors 150 that have lead receptacle coupling portions 450 and feedthrough coupling portions 460. A removable tab element 470 connects the conductors 150 of the pin assembly 440. Removable tab element 470 may be made of any material, but for ease of manufacture is preferably made of the same material as the conductive elements 150. Pin assembly 44 may be molded, stamped, or the like. A line of weakening may be the mechanism for removing tab element 470 from the rest of the pin assembly 440.

Pin assembly 440 depicted in FIGS. 14-15 is configured such that receptacle coupling portions 450 may be attached and electrically coupled to conductive portions 140 of two lead receptacles 120. Of course, pin assembly configurations that may be attached to any number of receptacles are contemplated. Once attached, e.g. by welding, pin assembly 440 serves to hold the first and second lead receptacles 120 in a somewhat rigid relative position until tab element 470 is removed. Due to the maintained spatial orientation, placement of receptacles 120 with attached lead frame pin assembly 470 into recess 300 of connector block header housing 45 is facilitated. The structural rigidity and ease of placement of receptacles 120 with attached lead frame pin assembly 440 into recess 300 may be further facilitated by the presence of alignment pins 380 (not shown in FIG. 14).

After placing the receptacles 120 in the recess 300 of header housing 120 (530), the receptacles 120 are secured to the housing 45, e.g. with adhesive or via anchor element 210 (540). The tab element 470 and alignment pins 380 may then be removed (550, 560). Header 440 may be attached to device housing 15 and feedthrough coupling portions 460 of conductors 150 may be electrically coupled to device feedthroughs 160 (570, 580). Medical adhesive or other suitable biocompatible polymer, such as liquid silicone rubber, may be used to fill voids between pin assembly 440, header housing 45, and receptacles 120 and to electrically insulate receptacles 120, conductors 150 and feedthroughs 160. Due to the rigidity of the header housing 45 and tight tolerances afforded thereby, the adhesive backfill may be preformed at high temperature and pressure, reducing manufacturing time and cost. A cover (not shown) may be attached to housing 45 and disposed over the adhesive backfill. In an embodiment, the cover is attached to housing by a hinge.

Costs associated with the manufacture of devices with connection headers made according to the process described above have been found to be reduced due in large part to decreased manufacturing time. In addition, reduced feed through failure and improvement in lead insertion force have been observed with such devices.

One of skill in the art will understand that components or steps described herein regarding a given embodiment or set of embodiments may readily be omitted, substituted, or added from, with, or to components or steps of other embodiments or sets of embodiments, as appropriate or desirable.

Thus, embodiments of CONNECTOR HEADER FOR IMPLANTABLE MEDICAL DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A connector header for an implantable medical device, the connector header comprising:
   a housing formed of a plastic material having a modulus or rigidity of 100 ksi or greater, the housing defining an opening for insertion of a lead, wherein a side opening is formed in a wall of the housing, the side opening extending from an interior surface of the housing to an exterior surface of the housing;
   a lead receptacle having an electrically conductive element operably couplable to a feedthrough of the implantable medical device, the lead receptacle being in communication with the opening and being disposed within the housing such that an electrical contact of the lead is electrically couplable to the electrically conductive element of the receptacle when the lead is inserted into the receptacle;
   a receptacle anchor element for securing the lead receptacle to the housing, the anchor element being operably coupled to the receptacle and at least a portion of the anchor element extending into the side opening; and
   a securing element disposed on the exterior surface of the housing at the side opening and connected to the receptacle anchor element, securing the lead receptacle relative to the housing.

2. The connector header of claim 1, wherein a portion of the housing defines a recess in an interior of the housing, the recess configured to receive the lead receptacle.

3. The connector header of claim 1, wherein the securing element is welded to the receptacle anchor element.

4. The connector header of claim 1, wherein the anchor element comprises an opening configured to operably engage a set screw.

5. The connector header of claim 1, wherein receptor anchor element comprises a mating region disposed in a complementary mating region formed by the housing.

6. The connector header of claim 1, wherein the electrically conductive element of the lead receptacle comprises the anchor element.

7. The connector header of claim 1, further comprising a reinforcement member molded in the housing, the reinforcement member positioned to be operably couplable to a bracket of the implantable medical device.

8. The connector header of claim 7, wherein the reinforcement member is formed of the substantially the same material as the bracket.

9. The connector header of claim 7, wherein the reinforcement member is formed of titanium.

10. The connector header of claim 1, wherein the housing is formed of polysulfone.

11. The connector header of claim 1, wherein the housing is formed of a plastic material having a modulus or rigidity of 200 ksi or greater.

12. The connector header of claim 1, wherein the housing is formed of a plastic material having a modulus or rigidity of 300 ksi or greater.

13. The connector header of claim 1, further comprising a plug placed externally into the side opening and configured to isolate the anchor element from body fluid when the header is implanted in a patient.

14. An implantable medical device comprising:
   a device housing;
   electronics disposed in the housing;
   an electrical feedthrough element operably coupled to the electronics and extending through a wall of the housing; and
   a connector header connected to the device housing and having
      (i) a header housing formed of a plastic material having a modulus of rigidity of 100 ksi or greater, the header housing defining an opening for insertion of a lead, wherein a side opening is formed in a wall of the header housing, the side opening extending from an interior surface of the header housing to an exterior surface of the housing, and
      (ii) a lead receptacle having an electrically conductive element operably coupled to the feedthrough element, the lead receptacle being in communication with the opening and being disposed within the header housing such that an electrical contact of the lead is electrically couplable to the electrically conductive element of the receptacle when the lead is inserted into the receptacle,
      (iii) a receptacle anchor element for securing the lead receptacle to the housing, the anchor element being operably coupled to the receptacle and at least a portion of the anchor element extending into the side opening, and
      (iv) a securing element disposed on the exterior surface of the housing at the side opening and connected to the receptacle anchor element, securing the lead receptacle relative to the housing.

15. The implantable medical device of claim 14, wherein at least a portion of the connector header housing is in contact with the device housing.

16. The implantable medical device of claim 14, wherein the securing element is welded to at least a portion of the anchor element.

17. The implantable medical device of claim 14, wherein the anchor element forms at least a part of a set screw block.

18. The implantable medical device of claim 14, wherein at least a portion of the anchor element is the conductive element of the lead receptacle.

19. The implantable medical device of claim 14, wherein the connector header comprises a reinforcement member molded into the header housing, the reinforcement member being operably coupled with a bracket of the device.

20. The implantable medical device of claim 19, wherein the reinforcement member is formed of titanium.

21. The implantable medical device of claim 19, wherein the header housing is formed of polysulfone.

22. The implantable medical device of claim 14, further comprising a plug placed externally into the side opening and configured to isolate the anchor element from body fluid when the device is implanted in a patient.

* * * * *